United States Patent [19]

Coleman et al.

[11] 4,097,384
[45] Jun. 27, 1978

[54] PROCESS FOR URANIUM ISOTOPE SEPARATION

[75] Inventors: John H. Coleman, Locust Valley, N.Y.; Tobin J. Marks, Evanston, Ill.

[73] Assignees: Northwestern University, Evanston, Ill.; Plasma Physics Corporation, Locust Valley, N.Y.

[21] Appl. No.: 668,829

[22] Filed: Mar. 22, 1976

[51] Int. Cl.² .......................... B01J 1/10; B01K 1/00
[52] U.S. Cl. .......................... 250/527; 204/DIG. 11; 204/157.1 R; 204/158 R
[58] Field of Search .................. 204/157 R, DIG. 11; 250/527

[56] References Cited

U.S. PATENT DOCUMENTS

| | | | |
|---|---|---|---|
| 3,904,500 | 9/1975 | Jensen | 204/DIG. 11 |
| 3,937,956 | 2/1976 | Lyon | 204/DIG. 11 |
| 3,941,670 | 3/1976 | Pratt | 204/DIG. 11 |
| 3,951,768 | 4/1976 | Gurs | 204/DIG. 11 |
| 3,983,020 | 9/1976 | Moore et al. | 204/DIG. 11 |
| 4,020,350 | 4/1977 | Ducas | 204/DIG. 11 |
| 4,024,217 | 5/1977 | Wexler et al. | 204/DIG. 11 |

OTHER PUBLICATIONS

Letokhov, Science, vol. 180, No. 4085, (4 May 73), pp. 451–455.

*Primary Examiner*—Howard S. Williams
*Attorney, Agent, or Firm*—Michael G. Berkman

[57] ABSTRACT

Separation of $U^{235}$ and $U^{238}$ isotopes by converting a mixture of these isotopes to organic compounds or to silicon compounds and then irradiating the isotope compounds selectively to change their chemical (and/or physical) properties, thereby to facilitate separation. In a preferred embodiment of the invention the uranium compounds are selected from the group having a chemical moiety R bonded directly to the U atom, the U-R bond having a fundamental, overtone, or combination virbational absorption frequency between 900 and 1100 $cm^{-1}$. The selected U mixture is then irradiated with a frequency-selective $CO_2$ laser.

11 Claims, 3 Drawing Figures

PROCESS FOR URANIUM ISOTOPE SEPARATION

BACKGROUND OF THE INVENTION

Isotope separation is an area of profound importance not only to chemists and physicists but to the entire populace as well. The use of infra-red lasers to separate isotopic species is suggested in the prior art. Described techniques involve selectively exciting gaseous molecules of a given isotope with intense, highly monochromatic laser radiation. It is required that the frequency of the radiation be coincident with a fundamental, combination, or overtone in the vibrational spectrum of the molecule. The vibrational excitement of the molecules may lead to spontaneous decomposition, or it may be necessary to introduce a second agent, which reacts selectively with the excited species. In some cases, simultaneous laser and ultraviolet or visible radiation have been employed. In all cases, the objective is selectively to transform the molecules of a single isotope into an enriched material which can be separated (on the basis of solubility, volatility, electrical charge, etc.) from the molecules containing the other isotope(s). To prevent energy transfer between isotopically different molecules, it may be desirable to operate at low pressures and/or to add an inert diluent.

The above concepts have been proposed for the photoexcitation separation of the uranium isotopes $U^{235}$ and $U^{238}$. Robieux, U.S. Pat. No. 3,443,087, describes the selective ionization of $UF_6$ by a combination of infra-red (IR) and ultra violet (UV) laser irradiation to facilitate electrostatic separation of $U^{235}$ in the vapor phase, and Belgian Pat. No. 821,823 describes selective dissociation of $UF_6$ by a combination of IR and UV, facilitating chemical separation of $U^{235}$.

However, the fundamental vibrational resonance frequencies of $UF_6$ are 624 $cm^{-1}$, and 186 $cm^{-1}$, values which are not presently available from electrically pumped transitions in gas lasers. Semiconductor lasers are available which can be tuned to this frequency, but their output power is limited to fractions of a watt. This low power results in an intensity that is insufficient for multiphoton absorption to cause dissociation. Any reactions induced would occur at low rates which are impractical for production processes. Other prior art separation processes such as those in UK Pat. No. 1,284,620 describe the method of isotope separation by selectively stimulating chemical reactions effected by irradiating an isotope mixture with a laser frequency corresponding to the vibrational absorption frequency. Specifically, it is there disclosed to use a $CO_2$ laser in combination with the molecules $UF_6$, $UF_nCl_{6-m}$, $UCl_6$, or $U(BH_4)_4$. However, none of these molecules is known to have fundamental vibration frequencies in the $CO_2$ laser output range! Since the most stable and reliable, and the most economical source of infra-red laser radiation is a carbon dioxide gas laser, the most effective range of which 9.2-11.0μ, 1086-909 $cm^{-1}$, the above molecules would not absorb sufficient radiation for usable excitation. None is reported to have fundamental or overtone metal-ligand vibrations in the appropriate region of the spectrum.

It is an important feature of the present invention that it teaches the use, in laser induced separations of uranium isotopes, of compounds having vibrational sensitivites accessible to a $CO_2$ laser.

In achieving the aims of the present invention, two properties are most desirable as initial criteria for the suitability of uranium compounds. In one embodiment, the compounds must be sufficiently volatile to be irradiated in the gas phase. In the second embodiment the compounds may be condensed from the gas phase in a matrix or applied as a solution. The molecules must have metal-ligand fundamental or overtone (preferably the former) vibrations in the region accessible to a $CO_2$ laser, i.e. 900–1100 $cm^{-1}$ in the preferred mode of irradiation. These criteria encompass a surprisingly wide range of compounds.

Coordination number and coordinative saturation appear to play a major role in determining the volatility of neutrally charged uranium compounds. In low oxidation states, e.g. +4 a uranium complex with non-bulky ligands will attempt to expand its coordination number beyond 4 by coordinating additional ligands, or, when these are unavailable, by forming ligand briding bonds to neighboring uranium ions. This leads to polymeric structure, high lattice energies, and low volatility. Two approaches can be used to circumvent this problem. In higher oxidation states, the uranium will have a smaller ionic radius, hence a smaller desired coordination number, and generally more ligands per metal ion. This usually leads to higher volatility. Another way to reduce intermolecular interactions is by employing sterically bulky ligands.

$UF_4$
(distorted square antiprism)

$UF_6$
(octahedral)

For example, in the alkoxide series, $U(OCH_3)_4$ is essentially non-volatile, insoluble, and is probably extensively associated in the solid state. In contract, $U[i-OC_3H_7]_4$ is more soluble and can be sublimed. Further confirmation of these concepts is found in $U(OC_2H_5)_5$ which is dimeric and rather volatile (boiling point 123°/0.001 mm pressure) and in $U(OC_2H_5)_6$ which is monomeric and even more volatile (boiling point 72°–74°/0.001 mm pressure). Thus, maximizing the oxidation state and the coordinative saturation are feasible approaches to increased volatility. Also important, but apparently less critical, is keeping the molecular weight as low as possible.

The foregoing discussion is believed to be relevant to reaction design for uranium iostope separation. One attractive strategy is to employ those laser-induced reactions which disassociate a ligand (or ligands) from the uranium, or which promote the substitution of a less bulky ligand. Starting with, for example, a U(VI) compound, laser promoted homolytic $UL_6 \rightarrow UL_5 + L\cdot$ $UL_5 \rightarrow UL_4 + L\cdot$ cleavages would reduce the uranium to the accessible +5 then +4 oxidation states. The $UL_5$ and $UL_4$ species are entities markedly less volatile than $UL_6$ and are separable. Alternatively, reactions such as $$UL_4 \rightarrow UL_4^* \xrightarrow{L'} UL_3L' + L$$

produce a U(IV) complex with different properties (e.g. volatility, solubility) than $UL_4$, since the L' is less bulky and may also form intermolecular bridges.

The compounds selected for use in the first embodiment must be stable to the thermal conditions necessary to volatalize them. In the Pearson terminology, uranium is a "hard" acid. It will have the greatest affinity for negatively charged, non-polarizable ligands. Such qualitative rules are relevant in developing syntheses and also in promoting, via laser irradiation, ligand substitution reactions. Fortunately, many of the properties which impart volatility afford, in addition, some resistance to thermal degradation. Studies of the mechanism of thermal decomposition of several classes of uranium organometallics indicate that corrdinative saturation of the uranium ion can greatly retard thermal decomposition. This presumably arises because immobilization of the coordination sphere blocks the lower energy pathways for thermolysis. Thus, the approaches which should foster higher volatility are, in addition, reasonable initial approaches to enhance thermal stability. Such concepts clearly illustrate that decompposition of the desired molecules by energetic photons facilitates separation from undecomposed molecules by the resulting differences in chemical and physical properties.

DESCRIPTION OF PREFERRED EMBODIMENTS

The following is a partial enumeration of useful classes of compounds, for the purposes of the present invention. The frequency of the metal-ligand stretching (and to a lesser extent, deformation) fundamental is important in the practice of the invention. The magnitude of the frequency difference in $\nu\ 238_{U-X}$ versus $\nu\ 235_{U-X}$ will depend on the particular molecular system. For uranyl complexes ($O=U^{+2}=O$) the difference should be ca. $0.7\ cm^{-1}$ for the antisymmetric $O=U=O$ stretch. Application of the Teller-Redlich product rule yields a value for the $T_{lu}$ U-O stretching mode of ca. $1.5\ cm^{-1}$ in $U(OCH_3)_6$, treating the methoxy ligands as point masses (a crude qualitative approximation). The most accurate analysis of metal ligand fundamentals is through high resolution metal isotopic substitution studies, an area which has recently seen rapid development.

A number of known volatile uranium complexes, not suggested for such use in the literature, are, in accordance with the invention, employed for the laser-induced separation of uranium isotopes. These compounds have metal-ligand fundamental or overtone vibrations in the spectral region accessible to a $CO_2$ laser, and, as herein disclosed, are susceptible to isotope-selective excitation and interception. Arranged by class, compounds useful in the practice of the invention include the following:

A. Borohydride-Organo Complexes

These complexes of the $BH_4^-$ ligand have been found to have a tridentate metal-ligand geometry. Under $C_{3v}$ local symmetry, the $A_1$ and E bridging modes, which are believed to have considerable $\nu$ M-H character, occur in the region ca. $1100-1230\ cm-1$. All have sufficient volatility to make them attractive. Examples are given below.

| |
|---|
| $U(BY_4)_4$ |
| $H_2C(C_5H_4)_2U(BY_4)_2$ |
| $(C_5H_5)_3\ U(BY_4)$    (Y = H,D) |
| $(C_5H_5)_3\ U(BY_3C_2H_5)$ |
| $(C_4H_4N)_3\ U(BY_4)$ |

Most of these complexes can be prepared by displacing halide with $BH_4^-$ or $BD_4^-$ in an ethereal solvent. Indeed, we have found borohydride derivatives to be some of the most accessible for a number of organoactinide systems studies. Additional volatile derivatives are prepared by sequences such as, $$U(OR)_n \xrightarrow{HCl} U(OR)_{n-1}Cl \xrightarrow{NaBH_4} U)OR0_{n-1}BH_4$$

In several of the compounds, for example $U(BH_4)_4$, the desired normal mode is above the frequency accessible to the $CO_2$ laser [for $U(BH_4)_4\ \nu = 1230\ cm^{-1}$]. Deuteration shifts this absorption to ca. $926\ cm^{-1}$. Deuterated compounds are accessible via commercially available $NaBD_4$ or $LiBD_4$.

B. Uranyl Complexes

These are complexes which incorporate the $O=•U=O$ functionality, usually in a pantagonal (A) or hexagonal (B) bipyramidal arrangement (a few octahedral examples are also known). The antisymmetrically coupled $\nu\ O=U=O$ stretching vibration usually occurs in the region $910-940\ cm^{-1}$.

A.                              B.

Another compound for laser irradiation is uranyl superphthalocyanine, prepared in a template reaction as shown below.

$M = UO_2^{+2}$

This compound has very high chemical and thermal stability and sublimes in vacuo at 400°. Still other organic "monomers" providing macrocyclic uranyl complexes of lower molecular weight, and greater volatility include:

Uranyl alkoxides, $UO_2(OR)_2$, also reported in the literature, are generally of low volatility, and are particularly suited for the second embodiment. Complexes with bulky fluorinated alcohols are also useful in the practice of the invention. While known uranyl β-diketonates are not appreciably volatile, very bulky ligands such as fod, shown below, complexed to uranium are of interest.

Also, aluminum alkoxide ligands impart volatility. A possible route to such complexes for U(VI) is,

C. Uranium Alkoxides and Siloxides

Complexes with $OR^-$ ligands may be prepared for uranium on a large scale and in a variety of oxidation states. Many are quite volatile; some are distillable liquids. The known analogous silicon compounds are also appreciably volatile. Representative species are shown below, and it is apparent that they offer a wide flexibility in terms of possible variation of oxidation state, symmetry, and volatility.

| | |
|---|---|
| $U(OR)_4$ | $U(OSiR_3)_4$ |
| $U(OR)_5$ | $U(OSiR_3)_5$ |
| $U(OR)_6$ | $U(OSiR_3)_6$ |

R = variety of organic groups

A U-O fundamental (except possibly for uranium in the +6 oxidation state) will not absorb in the desired frequency region. For example, the Ti-O stretches in Ti-$(OCH_3)_4$ have been assigned at 588 and 553 cm$^{-1}$, those in $Ti(OC_2H_5)_4$ at 625 and 500 cm$^{-1}$, and those in Nb(O-Et)$_5$ at 571 cm$^{-1}$. Though the fundamental U-O stretches in the aforementioned alkoxides may not be in the $CO_2$ laser range, overtones are. The fundamental U-O stretch occurs in the region 460–550 cm$^{-1}$. Hence, the first overtone is in the region 920–1100 cm$^{-1}$. By appropriate selection of ligands to "tune" the symmetry and various force constants, it is possible to bring a U-O overtone or combination band into Fermi resonance with another fundamental (e.g. $\nu$ C-O $\approx$ 1000 cm$^{-1}$), thereby increasing the excitation cross section. In addition, high power lasers operative at the U-O fundamental frequencies are expected to be available in the near future.

The uranium alkoxides also appear to be excellent precursors to other derivatives. Typical reaction schemes to introduce a variety of new ligands are shown below.

R = alkyl group

Mixed complexes in which one or more of the OR or $OSiR_3$ groups is replaced by a β-diketonate, a borodeuteride, or an alkyl group are within the concept of the present invention.

D. Uranium Alkyl Compounds

These compounds include complexes of the formula $L_n UR_{n-4}$ where $L=C_5H_5$, an alkoxide or siloxide, or borodeuteride and R is an alkyl (e.g. methyl, ethyl, isopropyl, t-butyl, benzyl, neopentyl) or aryl (e.g. phenyl) group. The U-C stretching - vibration occurs in the region of 500 cm$^{-1}$. Thus, the first overtone is in the region of 1000 cm$^{-1}$. Uranium alkyl compounds are thermally stable only if sufficient coordinative saturation is present to hinder various intramolecular decomposition processes. Thus $(C_5H_5)_3$ UR compounds (with π-bonded $C_5H_5$ ligands) possess rather high thermal stability. For R= methyl or vinyl, the complexes are sublimable.

X-ray structure of $(\eta^5-C_5H_5)_3U(-C\equiv CC_6H_5)$

Systems such as $(C_5H_5)_3UR$ offer the attractive feature that products of a homolytic laser-induced cleavage would be $(C_5H_5)_3U$, which is nonvolatile, and R-radicals, which could be scavenged. Other attractive uranium alkyl systems are presented below.

THF = tetrahydrofuran

Particularly interesting, in terms of imparting thermal stability, are bulky R groups (e.g. t-butyl), those without $\beta$-hydrogen atoms (e.g. tri-methylsilylmethyl) and chelating alkyls (e.g. those derived from 1, 4-dilithiobutane).

The stability of $W(CH_3)_6$ suggests the utilization of $U)CH_3)_6$, which is expected to be quite volatile.

E. Uranium Amides

The diethylamide of uranium $U[N(C_2H_5)_2]_4$ is volatile enough to be distilled or sublimed. Until recently, it was the only known uranium dialkylamide. Since the U-N stretch falls in the 500 cm$^{-1}$ region, the first overtone is in the region of 1000 cm$^{-1}$. The amido complexes of uranium contain the U-NR$_2$ functionality; examples include $U(NR_2)_4$, $L_nU(NR_2)_{n-4}$ where L = B diketonate, alkoxide or siloxide, alkyl group, or borodeuteride. Some approaches to a variety of compounds are proposed below.

The existence of $W[N(CH_3)_2]_6$ is impetus to investigate uranium oxidation states higher than +4.

In the above cases, the complexes may be irradiated in the gas phase or in the frozen solid phase at the fundamental, combination, or overtone metal (either $U^{238}$ or $U^{235}$) - ligand frequency, with a high power CO$_2$ gas laser. This is carried out both with and without simultaneous ultraviolet or visible irradiation. Reactive agents such as methanol, styrene, thiols, etc. can also be added to trap the excited molecules. In the first embodiment, the reactions are conducted preferably at low pressures, and it is possible to add an inert diluent such as methane, neon, argon, etc. In all cases, the selectively excited molecules react to form an iostopically enriched (in $U^{238}$ or $U^{235}$ depending on the irradiation frequency) product which is chemically different from the starting material. The product is then isolated from the starting materials on the basis of volatility, solubility, and/or electrical charge.

It is also possible, in accordance with the second embodiment of the present invention, to effect isotopic substitution by condensing or spraying the proposed compounds in an appropriate matrix at cryogenic temperatures. Selective excitation, as proposed for the gas phase procedures, is preferably carried out with a CO$_2$ laser, but other tunable, stable infra-red lasers may be used. The matrix is designed to react with the selectively excited uranium compounds. Suitable matrix components include alcohols, ketones, thiols, styrene, organic nitroxides, etc. Again, the reaction products differ sufficiently from the starting materials to allow separation when the matrix is warmed to ambient temperature.

BRIEF DESCRIPTION OF THE DRAWING

The present invention will be more fully described with reference to the drawings depicting suitable apparatus for effectuating the method of the invention and in which.

DESCRIPTION OF THE APPARATUS AND TECHNIQUES

Figure 1:
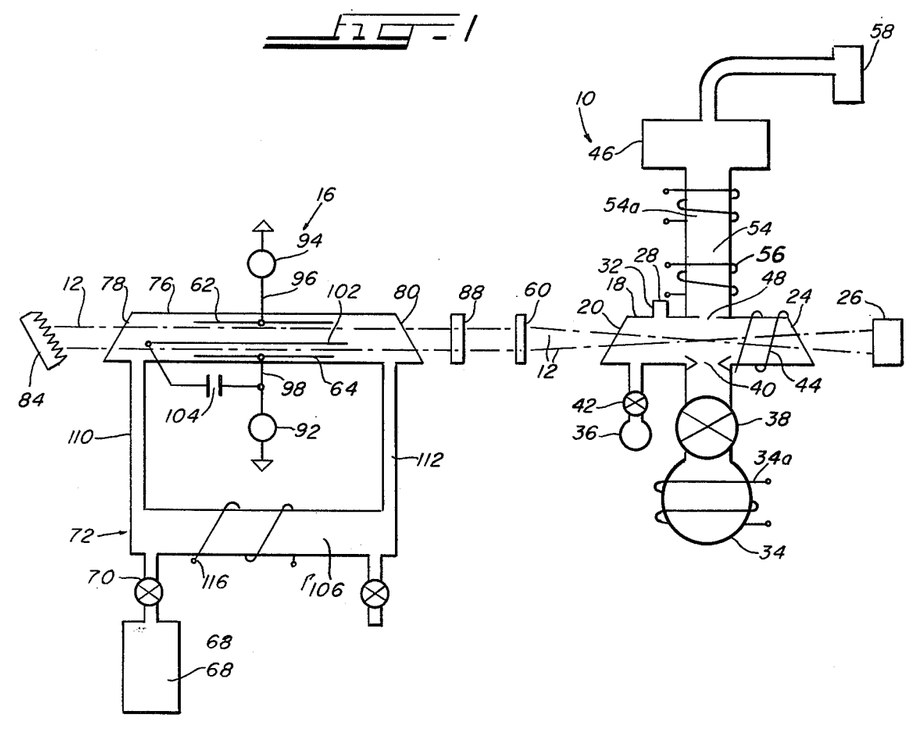
FIG. 1 illustrates one embodiment of the invention in which a pulsed CO$_2$ laser, controlled in frequency and intensity, is used to irradiate a gaseous U-organic isotope mixture.

Referring now more particularly to FIG. 1 of the drawing, a gaseous mixture of $U^{235}$ and $U^{238}$ incorporated in a U-organic compound, for example, a uranium alkoxide $U(OEt)_6$ is irradiated in a reactor 10 by a laser beam 12 from a pulsed CO$_2$ laser source 16. The reactor includes a one meter long monel reaction tube 18 having an entry window 20 for entry of the laser beam 12 and an exit window 24 for exit of the beam 12. The beam entry and exit windows 20, 24 may be of NaCl or other suitable materials such as ZnSe that transmit the 9–11 micron CO$_2$ laser radiation. The windows 20, 24 are positioned at the Brewster angle to the beam 12 to minimize loss of beam energy. A photo-detector 26 monitors the unabsorbed portion of the beam 12, and a monitor window 28 of quartz, connected by a side tube 32 to the reaction tube 18, may be used to monitor the visible and UV fluorescence from the reaction. The U-organic composition is stored in a reservoir 34, fitted with a heat exchange coil 34a, and a reactive or buffer gas may be stored in a second reservoir 36.

The U-organic composition, (or the U-silicon composition) is introduced into the reaction tube 18 through a metering valve 38 which may incorporate a converging-diverging nozzle 40 for expansion cooling, designed as is well known in the art to provide a velocity of approximately Mach 1 or larger. A reaction or buffer gas in reservoir 36 is introduced (when desired) into the reaction tube 18 through a second metering valve 42. A heating coil 44 adjusts the temperature in the reactor 18 for the desired vapor pressure. A vacuum pump 46 exhausts the gases in the reaction tube 18 through an aperture 48, to a second chamber or zone 54 the temperature of which is controlled by a heat exchanger 56. A third chamber or zone 54a may be used to condense unreacted components as well as volatile by-products. Pump 46 exhausts into a storage tank 58. The tetra alkoxide, U(OEt)$_4$ is a principal reaction product, together with organic fragments. The less volatile tetra alkoxide is then separated from the more volatile constituents of the mixture to achieve the desired isotope enrichment. A focusing lens 60 focuses the laser beam 12 through the entry window 20 to a spot on the optical axis of the reaction tube 18 to position the reaction above nozzle 40 of the valve 38.

The laser source 16 uses a pulsed electrical discharge between a pair of bronze electrodes 62, 64 to attain output power between the limits of $10^4$ and $10^{10}$ watts per cm$^2$. The upper value of beam intensity is limited in some cases by breakdown of the gases and formation of a plasma. The electrodes 62, 64, in a preferred embodiment of the invention, are 50 cm long × 2 cm wide and are separated by 1 cm. The lasing gas, which may be a 1,1,8 molar mixture of $CO_2$ $N_2$,He stored in a pressurized tank 68 is introduced through a reducing valve 70 into the circulating and cooling system 72 of laser source 16. The electrodes 62, 64 are symmetrically positioned above and below the axis of an acrylic laser tube 76. The tube ends are sealed by Brewster angle, NaCl end windows 78, 80. An optical resonator is formed between an adjustable grating 84 and a 95% reflecting germanium (Ge) mirrow 88 which are centered about the optical aXIS (which is slightly off-set from the center axis of the electrodes 62, 64 when the beam passes through the end windows 78, 80). Depending on whether a stable or unstable resonator is desired, the Ge mirror 88 may be convex, flat, or concave, as presented to the grating 84. The grating 84 acts as a plane, frequency-selective mirror which is adjusted for the particular U-organic used. The grating 84 and the Ge mirror 88 may be positioned inside the laser tube 76 eliminating the end windows 78, 80. However wide mirror spacing is desired to improve frequency characteristics.

Electrical power to the electrodes 62, 64 is supplied by a power supply 92, 94, through suitable leads 96, 98. The electrical pulse from supply 92, 94 is a fast rise-time pulse of typical magnitude 47 KV per cm of spacing between the electrodes 62, 64 and per atmosphere of lasing gases. The power supplies 92, 94 may be a Blumlein or equivalent design with low-inductance circuit elements. Alternatively a commercial, triggered spark-gap may be used for the power supply 92, in which case the lead 96 is connected directly to ground eliminating supply 94.

To facilitate a uniform glow discharge at high lasing gas pressures in the laser tube 76, a thin (0.007 inch) tungsten wire 102 is positioned at mid-plane but outside the edges of the electrodes 62, 64 and connected through a small capacitor 104 (typically 50 pF or less) to the lead 98. Thus, the rising voltage from the power supply 92, which increases the potential difference between the electrodes 62, 64, also increases the potential difference between the wire 102 and the electrode 62. However, the Townsend breakdown voltage between the wire 102 and the electrode 62 is adjusted to be lower than between the electrodes 62, 64 thereby causing limited breakdown and preionization of the lasing gas prior to breakdown between the electrodes 62, 64. Other pre-ionization circuits may be used such as naked spark-gaps positioned outside the electrodes 62, 64 along the mid-plane to UV-irradiate the gap between the electrodes 62, 64. Also, a low ionization-potential liquid such as tri-butylamine may be applied to the electrodes 62, 64 to reduce sparking.

Hot lasing gases from the gap between the electrodes 62, 64 are recirculated and cooled through a cooling tube 106 of the refrigerator 72 by ducts 110, 112 by means of a pump (not shown). A cooling coil 116 extracts the heat, from the lasing gases, added by power absorbed from the power supply 92 during the electrical discharge. The ducts 110, 112 are ideally located to circulate lasing gases directly through the space between the electrodes and may use a diffuser if turbulence is required to stabilize the discharge.

The most convenient operating pressure of lasing gases in the laser tube 76 is atmospheric. However, the value can be above or below one atmosphere, depending on desired output characteristics. In some cases it may be necessary to raise the pressure to attain tunability above the natural transitions as broadening of the $CO_2$ lines increases 3GHz per atmosphere up to 10 atmospheres where $CO_2$ laser lines overlap.

Thus in operation, the laser source 16 is switched on the aligned with the optical axis of the reaction tube 18 of the reactor 10. To obtain the proper output frequency selection of the laser source 16, the reaction tube 18 is evacuated and backfilled with U-organic compound enriches in $U^{235}$. Absorption is noted while laser lines are selected with the grating 84. The U-organic feedstock in reservoir 34 is then admitted through the reducing nozzle 40 and irradiated. Non-volatile reaction products are condensed in Chamber 54 and non-volatile products as well as reacted U-organic are condensed in a second cold zone 54a.

Of course, other U-organics may be used with the laser source 16 tuned by the grating 84 to the desired frequency and with the intensity selected to the proper value. In each case the reaction proceeds from the focal spot back up-stream toward the laser source 16 until the intensity falls below the minimum value.

Figure 2:
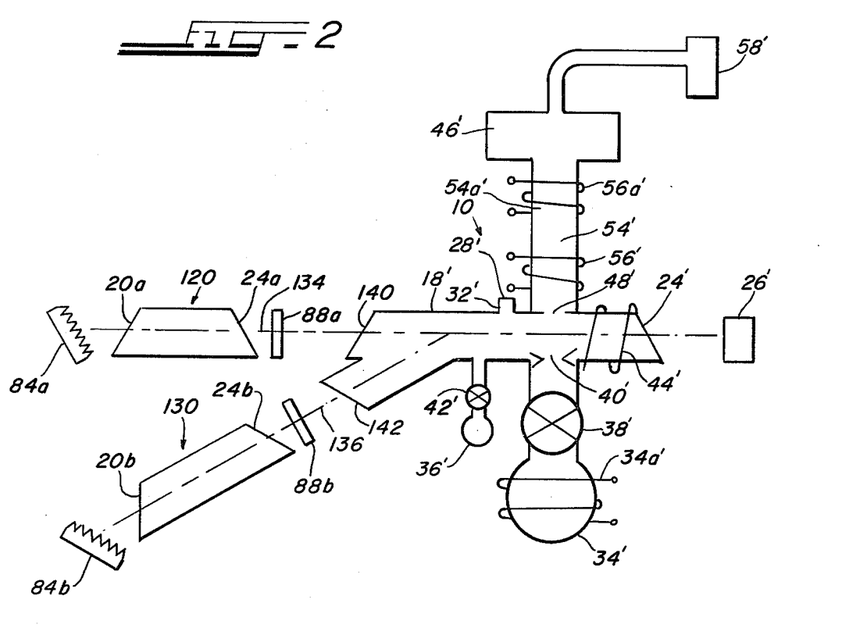
FIG. 2 illustrates a second embodiment in which the radiation from a CO$_2$ laser is combined with a UV source to irradiate a gaseous U-organic isotope mixture.

The apparatus of FIG. 2 differs from that of FIG. 1 primarily in the arrangement of the "laser source", two sources being used in the FIG. 2 embodiment. For the most part, the reactor of FIG. 2 is the same as for FIG. 1 and, therefore, the corresponding mechanical components of FIG. 2 are designated by "primes" (').

Referring now to FIG. 2, tunable $CO_2$ infra-red laser source 120 and tunable argon ion laser source 130 direct laser beams 134 and 136 through Brewster angle input windows 140 and 142 to a common focal spot. The second input window 142 is made from a silica or Vycor plate, transparent to UV and visible radiation while the remaining parts, designated with subscripts "a" and "b", of the two laser apparati are similar to those described with reference to FIG. 1. However, since fewer IR photons are required, sufficient intensity may be obtained from the laser source 120 without use of a focusing lens, which is omitted, or by means of a CW $CO_2$ laser with sufficient output intensity (power per unit area).

In operation, on proper frequency tuning, the laser source 120 excites the vibrational states in the U-organic compound and the laser source 130 raises the electronic states sufficiently to dissociate the desired chemical bond attached directly to the U atom or to stimulate a chemical reaction. Laser 130 may be replaced with a filtered Hg lamp or other UV source of sufficient intensity to dissociate the desired bond in the cases that sufficient isotope selectivity is obtained through vibrational excitation by irradiating with laser 120. A frequency doubler (not shown) may be used with the tunable laser 130, depending upon the particular U-organic.

Figure 3:
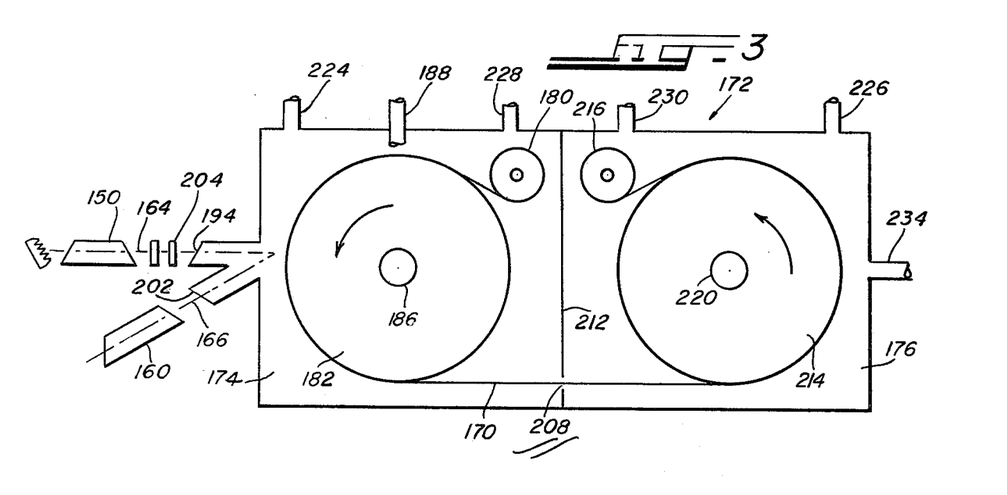
FIG. 3 illustrates a third embodiment in which lasers irradiate a solid-state U-organic isotope mixture frozen in a glassy matrix.

Referring to FIG. 3, laser sources 150 and 160 provide laser beams 164 and 166 to irradiate U-organics in the frozen solid state transported on a ribbon-like substrate 170 through a reaction chamber 172 between two adjacent irradiation sections 174, 176 in which the atmosphere may be controlled. Laser 160 may be replaced with a filtered Hg lamp or other UV source of sufficient intensity to dissociate the desired bond in the cases that sufficient isotope selectivity is obtained through vibrational excitation by irradiating with laser 150. In the irradiation section 174, the substrate 170, which may be thin stainless steel foil, is moved from a take-off spool 180 onto a hollow, rotating first drum 182 which is cooled by liquid $N_2$ injected through a hollow journal 186. A nozzle 188 sprays on U-organic such as $L_nUO_2$ where L is a macrocyclic ligand such as superphthalocyanine mixed with a matrix such as 3 methylpentane in the molar ratio of 1/100. Alternatively, the matrix may be selected from several gases or organic liquids or gases which do not absorb photons at the laser frequencies used and which do not broaden the U-organic vibrational absorption substantially. The frozen U-organic and matrix on the substrate 170 is irradiated by a beam 164, from a $CO_2$ laser source 150 transmitted through a NaCl window 194 (or $ZnSe_2$) and a beam 166 from an argon ion laser source 160 through a silica window 202. An auxiliary lens 204 may be used to focus the beam 164 onto the substrate 170 to increase its intensity. The $CO_2$ laser source 150 is tuned to the vibrational absorption frequency of the U-organic and the argon laser source 160 is tuned to the electronic absorption frequency to effect dissociation of the U-bond or to induce a reaction with a reactant such as $Cl_2$ incorporated in the matrix. Other reactants may be HCl, HI, etc. Alternatively, as in FIG. 1, the $CO_2$ laser source 150 may supply photons of sufficient intensity to cause dissociation of a U-bond. The limits of such intensity are between $10^4$ watts/cm$^2$ and $10^{10}$ watts/cm$^2$. In this case the argon laser source is not used. Subsequently, the substrate 170 containing the reaction products from irradiation and unreacted feestock is moved through a slit 208 in a section-separating partition 212 of the chamber 172 over a second hollow drum 214 and onto a takeup spool 216. The temperature of the drum 214 is controlled by introducing a fluid from a heat exhcnager, (not shown) through a hollow journal 220. The temperature of the second drum 214 is adjusted to raise the temperature of reaction products of the U-organic on substrate 170 to cause a reaction with the reactive material to facilitate separation. This temperature may be as low as a few degrees above the temperature of the first drum 182 or may be higher to facilitate separation of reaction products by their resulting volatility differences. The atmosphere in the chamber sections 174, 176 may be controlled by evacuation through pipes 224, 226 and backfilling through tubes 228, 230. Reactive material may be introduced through a tube 234 directly onto the moving substrate 170. The substrate 170 is then removed from the take up spool 216 and modified $U^{235}$-organic adhered thereto is chemically separated. Other U-organics may be used in all embodiments, provided a fundamental overtone or combination vibrational absorption occurs in the 900–1100 cm$^{-1}$ $CO_2$ laser output range. Also, tunable laser sources 130 and 160 may be tunable dye lasers with suitable frequency doublers (not shown), depending on the electronic energy levels of the U-L bond.

What is claimed is:

1. Apparatus for separating isotopes of a metallic element to provide an iostopically-enriched product, said apparatus comprising:
   reaction chamber means for retaining a chemical composition including a plurality of isotopic species of the metallic element,
   valve means for controlling introduction of the chemical composition into said reaction chamber means,
   means for controlling atmospheric composition within said reaction chamber means,
   temperature control means to regulate the temperature interiorly of said reaction chamber means,
   generator menas including power supply means for producing a beam of radiated energy,
   means including electrode means to direct said beam to impinge upon said chemical composition contained in said chamber means to interact with and to modify properties of said chemical composition so as to facilitate the separation of isotopic components thereof.

2. The apparatus as set forth in claim 1 and further comprising photo detector means for monitoring interaction of said beam with said composition.

3. The apparatus as set forth in claim 1 and further comprising reservoir means for storage of said chemical composition, and heat exchange means for regulating the temperature of the composition stored in said reservoir means.

4. The apparatus as set forth in claim 1 and further comprising a reservoir for storage of reaction and buffer gas, and valve means for regulating introduction thereof into said reaction chamber.

5. The apparatus as set forth in claim 1 and further comprising vacuum pump means for exhausting gases from said reaction chamber.

6. The apparatus as set forth in claim 1 wherein said generator means includes means for generating a tunable $CO_2$ infra-red laser.

7. The apparatus as set forth in claim 1 wherein said temperature control means comprises an expansion nozzle connected to said valve means and positioned in said reaction chamber means.

8. The apparatus as set forth in claim 1 wherein said generator means includes means for generating tunable infra-red radiation.

9. The apparatus as set forth in claim 1 wherein said generator means includes means for generating tunable infra-red radiation and for generating ultra violet radiation.

10. Apparatus for separating isotopes of a metallic element to provide an isotopically-enriched product, said apparatus comprising:
    generator means to produce a beam of radiated energy,
    irradiation chamber means disposed to receive a beam of radiated energy from said generator means,
    movable substrate means for supporting a composition to be irradiated,
    means for supporting and moving said substrate means and a composition including a plurality of isotopic species carried thereon through said irradiation chamber means,
    reaction chamber means and means communicating with said irradiation chamber means to permit passage of said substrate means therethrough from said irradiation chamber means to said reaction chamber means, drive means for propelling said substrate means through said reaction chamber means to facilitate interaction between the substrate-carried composition and a reactant contained in said reaction chamber means.

11. The apparatus as set forth in claim 10 and further comprising temperature control means for regulation of the temperature in said reaction chamber means.

* * * * *

UNITED STATES PATENT OFFICE
CERTIFICATE OF CORRECTION

Patent No. 4,097,384                    Dated  June 27, 1978

Inventor(s) JOHN H. COLEMAN and TOBIN J. MARKS

It is certified that error appears in the above-identified patent and that said Letters Patent are hereby corrected as shown below:

Column 4, line 34, delete "U) $ORO_{n-1}$" and insert -- $U(OR)_{n-1}$ --

Column 7, line 21, delete "$U)CH_3)_6$" and insert -- $U(CH_3)_6$ --

Column 11, line 45, delete "exhcnager" and insert --exchanger--

Claim 1, line 13, delete "menas" and insert --means--

Signed and Sealed this

Nineteenth Day of December 1978

[SEAL]

Attest:

RUTH C. MASON
*Attesting Officer*

DONALD W. BANNER
*Commissioner of Patents and Trademarks*